United States Patent [19]

Jennen et al.

[11] 4,101,696
[45] Jul. 18, 1978

[54] THERMOGRAPHIC PLATE FOR MEASURING TEMPERATURE DISTRIBUTIONS

[75] Inventors: Friedrich Jennen, Bergisch-Gladbach, Germany; Jean Tricoire, Paris, France

[73] Assignee: Troponwerke Dinklage & Co., Cologne, Germany

[21] Appl. No.: 709,991

[22] Filed: Jul. 30, 1976

[30] Foreign Application Priority Data

Aug. 19, 1975 [DE] Fed. Rep. of Germany ....... 2536773

[51] Int. Cl.$^2$ ............................................. G01K 11/12
[52] U.S. Cl. ........................................ 428/1; 73/356; 128/2 H; 350/351; 428/216
[58] Field of Search ............................ 73/356; 128/2 H; 350/160 LC; 428/1; 116/114.5; 23/230 LC

[56] References Cited

U.S. PATENT DOCUMENTS

| | | | |
|---|---|---|---|
| 2,524,286 | 10/1950 | Dreyer | 428/1 |
| 3,533,399 | 10/1970 | Goldberg | 73/356 |
| 3,617,374 | 11/1971 | Hodson | 73/356 |
| 3,830,224 | 8/1974 | Vanzetti | 73/356 |
| 3,847,139 | 11/1974 | Flam | 73/356 |
| 3,852,092 | 12/1974 | Patterson | 428/1 |
| 3,951,133 | 4/1976 | Reese | 73/356 |
| 3,993,809 | 11/1976 | Schranz | 73/356 |

*Primary Examiner*—Richard C. Queisser
*Assistant Examiner*—Denis E. Corr
*Attorney, Agent, or Firm*—Burgess, Dinklage & Sprung

[57] ABSTRACT

The thermographic plate consists of a carrier film, a latex-based optically inhomogeneous black layer applied thereto and of a layer containing liquid crystals. The thickness of the black layer amounts to between 4 and 18 μm. By virtue of this coordination of the thickness parameters, particularly high color intensity and hence correspondingly high image quality are obtained in the diagnosis of thermal anomalies.

8 Claims, 1 Drawing Figure

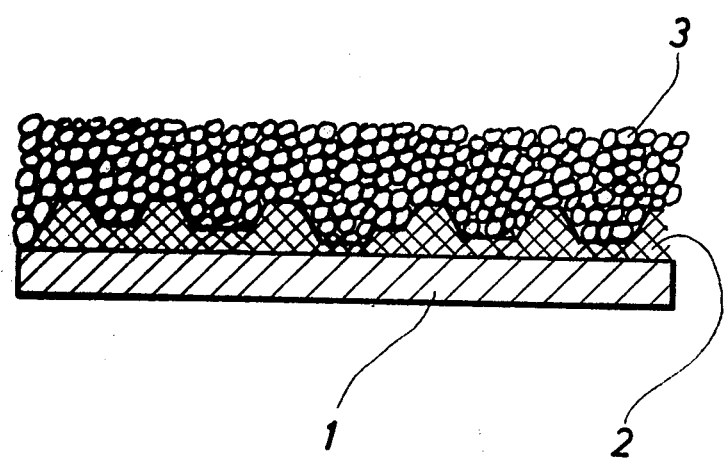

THERMOGRAPHIC PLATE FOR MEASURING TEMPERATURE DISTRIBUTIONS

This invention relates to a thermographic plate consisting of a carrier film, a latex-based optically inhomogeneous black layer with an overall thickness of less than 200 μm and a layer containing liquid crystals. Plates of this kind are used for visually displaying temperature variations on the surface of solid bodies. One important application is in medical diagnosis. With thermographic plates or film, it is possible to identify malignant tumours, obstructed blood vessels or other thermal anomalies.

The temperature-sensitive layer consists of a dispersion of cholesterol esters in a suitable binder. Cholesterol esters sow characteristic colour phenomena at a certain temperature. The properties of compounds of this class are described in detail in the literature, so that they will not be discussed in more detail here. The liquid crystals are highly sensitive to impurities and oxidation by atmospheric oxygen. For this reason, the cholesterol ester droplets are surrounded by a coating of gelatin or gum arabic (Mikroverkapselungstechnik, cf. for example German patent specification No. 1,648,266).

The liquid crystal layer is applied to a black layer. The function of the black layer is to absorb the light allowed through by the liquid crystals and reflected by the underlying carrier film. Accordingly, the liquid crystal layer is observed against a black background. If the black layer is too thin, the colour play of the liquid crystals can almost completely disappear. Thermoplastic films (for example polyethylene glycol terephthalate) are generally used as the carrier layer.

In medical diagnosis, the problem is visually to indicate minor differences in temperature, often less than 0.5° C, by means of the thermographic plate. In applications such as these, therefore, the thermographic plate has to reproduce as faithfully as possible the distribution of temperature on the surface with a resolution of less than 0.5° C. The definition or sharpness of a thermographic plate is determined on the one hand by its thermal conduction properties and on the other hand by its optical properties. The thermal conduction properties have a marked influence because the thermographic plate is placed with its uncoated surface on the parts of the body to be investigated. The heat has to diffuse from the surface of the skin through the carrier film and the black layer to the liquid crystal layer. It will readily be appreciated that any lateral diffusion of heat, i.e. parallel to the layer, will result in a reduction in sharpness. In unfavourable cases, more or less blurred colour structures are obtained which make it impossible to localise small anomaly regions. For this reason, lateral heat diffusion has to be kept to a minimum. U.S. Pat. No. 3,796,884 describes a thermographic plate in which the black layer has a "lattice-like structure". A "lattice-like structure" is essentially a structure which, in optical terms, may be regarded as a layer with statistically fluctuating transparency. This structure is said to promote the conduction of heat perpendicularly of the layer in comparison with the conduction of heat in the lateral direction. This black layer is formed by spraying on several coats of a black-pigmented latex.

The thermographic plate according to U.S. Pat. No. 3,796,277 has already been successfully used in medical diagnosis. However, further investigations have shown that, in many cases, image quality is unsatisfactory despite adequate sharpness. The explanation for this lies in the fact that, in addition to the thermal conduction parameters, the optical properties are a determining influence upon image quality. The optical properties of the thermographic plate are quantitatively graded by the colorimetric parameters of colour, saturation and lightness.

The object of the present invention is to improve the optical properties of the thermographic plate described at the beginning without at the same time affecting the favourable thermal properties which have hitherto been obtained. According to the invention, this object is achieved by virtue of the fact that the thickness of the black layer in the thermographic plate described at the beginning is in the range from 4 to 18 μm. The black layer is preferably built up on 4 to 6 latex coats of which each has a layer thickness of the order of 1 to 3 μm. The black layer advantageously consists of a latex formed by a copolymer of methacrylic acid methyl ester and acrylic acid ethyl ester.

A further development of the invention is characterised by the fact that the layer of liquid crystals is thicker than the black layer by a factor of 2 to 6.

It was not expected that an improvement in the optical properties would be obtained by reducing the thickness of the black layer. The absorption, and hence suppression of troublesome reflections from the carrier film is normally better, the greater the layer thickness of the black layer. The improved properties of the new thermographic plate in regard to colour, colour saturation and lightness are surprising when it is realised that a latex-based black layer as thin as this no longer forms a coherent pigment layer, but instead consists of individual islands on an otherwise transparent substrate. The statistically fluctuating optical transparency of this layer is readily visible under a microscope with 40-fold to 60-fold magnification. The favourable thermal properties (thermal conduction) remain unchanged.

The invention is described by way of example in the following with reference to the accompanying drawing which is a cross-section on an enlarged scale through the layer structure of a thermographic plate. The layer support consists of a polyethylene glycol terephthalate film 1 with a layer thickness of 6 μm. On top of this film 1 is the black layer 2 which also has an average thickness of 6 μm. It consists of a copolymer of methacrylic acid methyl ester and acrylic acid ethyl ester containing approximately 2 to 3% of carbon black as the black pigment and approximately 2 to 3% of silicon dioxide. The liquid crystal layer 3 is applied to the black layer 2. It consists of microencapsulated liquid cholesterol crystals dispersed in a binder. In this case the liquid crystal layer has a thickness of 30 μ. The layer thickness of the black layer is macroscopically measured. An eddy current layer thickness gauge with a contact surface area of a few mm² was used for this purpose. The measured layer thickness represents a form of average value of this surface.

In other embodiments, the thickness of the carrier film 1 varies from 5.8 to 10 μm, the thickness of the black layer from 4 to 12 μm and the thickness of the liquid crystal layer from 20 to 40 μm.

A thermographic plate of the kind described above can be produced as follows:

Using a spray gun, up to six coats of latex are successively sprayed, with intermediate drying, onto a thoroughly cleaned polyethylene glycol terephthalate film 1. The thickness of a single latex coating amounts on average to between 1μ and 3μ. The latex has the composition defined above and is dissolved (dispersed) in toluene. After the latex-based black layer 2 has been dried, the liquid crystal layer 3 is applied by means of a coating knife. Coating with a coating knife is standard practice in thin layer chromatography. The liquid crystals have a wet layer thickness of from 200 to 250 μm. During drying the thickness of the layer of liquid crystals can shrink by a factor of 5 to 10. Drying can either be carried out in the usual way at room temperature or accelerated by applying higher temperatures (30° to 40° C).

What we claim is:

1. A thermographic plate with an overal thickness of less than 200 μm consisting of a transparent carrier film, an intermediate latex-based black layer on said film and a layer containing liquid crystals disposed on the intermediate layer, the improvement comprising the black layer having an average thickness in the range of 4–18 μm and comprising an irregular array of individual black islands produced by spray coating a plurality of successive spray coats of latex with intermediate drying on the otherwise transparent carrier film, to provide a statistically fluctuating transparency.

2. A thermographic plate as claimed in claim 1, wherein the black layer is built up from 4 to 6 coats of latex of which each coat has a layer thickness of from 1 to 3 μm.

3. A thermographic plate as claimed in claim 2, wherein the latex consists of a copolymer of methacrylic acid methyl ester and acrylic acid ethyl ester with carbon black added as black pigment.

4. A thermographic plate as claimed in claim 1, wherein the latex consists of a copolymer of methacrylic acid methyl ester and acrylic acid ethyl ester with carbon black added as black pigment.

5. A thermographic plate as claimed in claim 4, wherein the layer containing liquid crystals is thicker than the black layer by a factor of from 2 to 6.

6. A thermographic plate as claimed in claim 1, wherein the layer containing liquid crystals is thicker than the black layer by a factor of from 2 to 6.

7. A thermographic plate as claimed in claim 6, wherein the carrier film has a thickness of from 5.8 to 10 μm, the black layer has a thickness of from 4 to 12 μm and the liquid cyrstal layer has a thickness of from 20 to 40 μm.

8. A thermographic plate as claimed in claim 1, wherein the carrier film has a thickness of from 5.8 to 10 μm, the black layer has a thickness of from 4 to 12 μm and the liquid crystal layer has a thickness of from 20 to 40 μm.

* * * * *